US011087939B2

(12) United States Patent
Tehlar et al.

(10) Patent No.: US 11,087,939 B2
(45) Date of Patent: Aug. 10, 2021

(54) DEVICE FOR INTERRUPTING NON-SHORT CIRCUIT CURRENTS ONLY, IN PARTICULAR DISCONNECTOR OR EARTHING SWITCH

(71) Applicant: ABB Power Grids Switzerland AG, Baden (CH)

(72) Inventors: Denis Tehlar, Zürich (CH); Martin Seeger, Oberentfelden (CH); Nitesh Ranjan, Wettingen (CH); Patrick Stoller, Illnau (CH); Raffael Buehler, Dübendorf (CH); Jan Carstensen, Waldshut-Tiengen (DE)

(73) Assignee: ABB Power Grids Switzerland AG, Baden (CH)

( * ) Notice: Subject to any disclaimer, the term of this patent is extended or adjusted under 35 U.S.C. 154(b) by 0 days.

(21) Appl. No.: 16/773,297

(22) Filed: Jan. 27, 2020

(65) Prior Publication Data
US 2020/0161064 A1 May 21, 2020

Related U.S. Application Data

(60) Division of application No. 15/783,183, filed on Oct. 13, 2017, now Pat. No. 10,553,376, which is a
(Continued)

(51) Int. Cl.
*H01H 33/52* (2006.01)
*H01H 33/12* (2006.01)
(Continued)

(52) U.S. Cl.
CPC ......... *H01H 33/122* (2013.01); *C07C 49/167* (2013.01); *H01H 33/182* (2013.01);
(Continued)

(58) Field of Classification Search
CPC ............ H01H 39/004; H01H 33/6646; H01H 33/666; H01H 79/00; H01H 33/32;
(Continued)

(56) References Cited

U.S. PATENT DOCUMENTS 3,048,683 A    8/1962 Haakon
3,514,563 A    5/1970 Stegmuller
(Continued)

FOREIGN PATENT DOCUMENTS

CN    88103437 A    12/1988
CN    1166680 A     12/1997
(Continued)

OTHER PUBLICATIONS

Chinese Patent Office, First Office Action, issued in corresponding Chinese application No. 201580080892.3, dated Nov. 15, 2018, 19 pp.
(Continued)

*Primary Examiner* — Truc T Nguyen
(74) *Attorney, Agent, or Firm* — Sage Patent Group

(57) ABSTRACT

The present invention relates to a device for interrupting non-short circuit currents only, and in particular relates to a disconnector, more particularly high voltage disconnector, or to an earthing switch, more particularly make-proof earthing switch, and further relates to a low voltage circuit breaker. The device comprises at least two contacts movable in relation to each other between a closed state and an open state and defining an arcing region, in which an arc is generated during a current interrupting operation and in which an arc-quenching medium comprising an organofluorine compound is present. According to the application, a counter-arcing component is allocated to the arcing region, the counter-arcing component being designed for counter-
(Continued)

acting the generation of an arc and/or being designed for supporting the extinction of an arc.

12 Claims, 4 Drawing Sheets

Related U.S. Application Data continuation of application No. PCT/EP2015/057964, filed on Apr. 13, 2015.

(51) Int. Cl.
| | | |
|---|---|---|
| *H01H 33/18* | (2006.01) | |
| *H01H 33/70* | (2006.01) | |
| *H01H 33/90* | (2006.01) | |
| *H01H 33/91* | (2006.01) | |
| *C07C 49/167* | (2006.01) | |
| *H01H 33/86* | (2006.01) | |

(52) U.S. Cl.
CPC ........ *H01H 33/7084* (2013.01); *H01H 33/86* (2013.01); *H01H 33/90* (2013.01); *H01H 33/91* (2013.01)

(58) Field of Classification Search
CPC ...... H01H 1/06; H01H 33/126; H01H 47/325; H01H 2003/268; H01H 33/12; H01H 33/18; H01H 33/185; H01H 33/36; H01H 33/59; H01H 33/7069; H01H 33/76; H01H 33/88; H01H 33/901; H01H 33/904; H01H 33/91; H01H 47/02; H01H 9/167
See application file for complete search history.

(56) References Cited

U.S. PATENT DOCUMENTS

| | | | |
|---|---|---|---|
| 3,832,505 A | 8/1974 | Wong | |
| 3,955,057 A | 5/1976 | Dabringhausen | |
| 3,991,292 A * | 11/1976 | Perkins | H01H 33/91 218/62 |
| 4,045,633 A | 8/1977 | Barkan | |
| 4,211,904 A | 7/1980 | Karrenbauer | |
| 4,359,616 A | 11/1982 | Ueda et al. | |
| 4,459,447 A * | 7/1984 | Arimoto | H01H 33/94 218/56 |
| 4,517,425 A | 5/1985 | Martin | |
| 4,841,108 A * | 6/1989 | Hamm | H01H 33/91 218/57 |
| 5,045,651 A * | 9/1991 | Seki | H01H 33/91 218/57 |
| 7,816,618 B2 | 10/2010 | Uchii | |
| 2006/0151438 A1* | 7/2006 | Urai | H01H 33/904 218/57 |
| 2008/0135817 A1 | 6/2008 | Luly et al. | |
| 2010/0219161 A1* | 9/2010 | Seeger | H01H 33/74 218/51 |
| 2012/0000753 A1 | 1/2012 | Faik | |
| 2013/0020285 A1 | 1/2013 | Schiffbauer | |
| 2014/0263187 A1 | 9/2014 | Yamada | |
| 2015/0021297 A1 | 1/2015 | Stoller | |
| 2015/0340179 A1 | 11/2015 | Aitken | |
| 2015/0357137 A1 | 12/2015 | Kubo | |
| 2016/0005559 A1 | 1/2016 | Kaneko | |
| 2016/0049269 A1 | 2/2016 | Gorablenkow | |
| 2016/0217956 A1* | 7/2016 | Kuroda | H01H 11/042 |
| 2017/0084412 A1* | 3/2017 | Bujotzek | H01H 1/385 |
| 2020/0373104 A1* | 11/2020 | Stacom | H01H 33/12 |
| 2020/0395180 A1* | 12/2020 | Galletti | H01H 1/385 |

FOREIGN PATENT DOCUMENTS

| | | |
|---|---|---|
| CN | 101238534 A | 8/2008 |
| CN | 201315287 Y | 9/2009 |
| CN | 102047365 A | 5/2011 |
| CN | 104488058 A | 4/2015 |
| DE | G8131053.6 U1 | 2/1986 |
| DE | 102009025204 B3 | 11/2010 |
| DE | 112012005206 T5 | 9/2014 |
| DE | 102013205945 A1 | 10/2014 |
| EP | 0476502 B1 | 1/1997 |
| EP | 2284854 A1 | 2/2011 |
| JP | H05-250966 A | 9/1993 |
| JP | H10-208595 A | 8/1998 |
| JP | 2003109481 A | 4/2003 |
| JP | 2004164994 A | 6/2004 |
| KR | 200306995 Y1 | 3/2003 |
| KR | 101053384 B1 | 8/2011 |
| WO | 2007016797 A1 | 2/2007 |
| WO | 2010142346 A1 | 12/2010 |
| WO | 2012080222 A1 | 6/2012 |
| WO | 2012080246 A1 | 6/2012 |
| WO | 2013153110 A1 | 10/2013 |
| WO | 2014187940 A1 | 11/2014 |
| WO | 2016102002 A1 | 6/2016 |

OTHER PUBLICATIONS

Chinese Patent Office, Second Office Action, issued in corresponding Chinese application No. 201580080892.3, dated Jun. 24, 2019, 12 pp.

European Patent Office, International Search Report & Written Opinion, issued in corresponding application No. PCT/EP2015/057964, dated Dec. 22, 2015, 12 pp.

* cited by examiner

DEVICE FOR INTERRUPTING NON-SHORT CIRCUIT CURRENTS ONLY, IN PARTICULAR DISCONNECTOR OR EARTHING SWITCH

CROSS REFERENCE TO RELATED APPLICATIONS

This application is a divisional of U.S. patent application Ser. No. 15/783,183, filed on Oct. 13, 2017, now U.S. Pat. No. 10,553,376, issued on Feb. 4, 2020, which is a continuation of § 371 national stage application of PCT International Application No. PCT/EP2015/057964 filed on Apr. 13, 2015, the disclosure and contents of which are incorporated by reference herein in their entirety.

The present invention relates to a device for interrupting non short-circuit currents only, in particular to a disconnector, more particularly a high voltage disconnector, or an earthing switch, more particularly a make-proof earthing switch, as well as to a medium voltage or high voltage gas-insulated switchgear (GIS) comprising such a device. The present invention further relates to a low voltage circuit breaker.

Dielectric insulation media in liquid or gaseous state are conventionally applied for the insulation of an electrically conductive part in a wide variety of apparatuses, and in particular also in GIS or components thereof.

In medium or high voltage metal-encapsulated switchgears, for example, the electrically conductive part is arranged in a gas-tight housing, which defines an insulating space, said insulation space comprising an insulation gas and separating the housing from the electrically conductive part without allowing electrical currents to pass through the insulation space.

For interrupting the current in e.g. high voltage switchgears, the insulating medium further functions as an arc-quenching medium (or arc-extinction medium). This is e.g. also the case in a disconnector or in an earthing switch, in which the arc generated during current interruption is extinguished under free-burning conditions, meaning that the arc-quenching medium is not actively blown towards the arc.

In conventional gas-insulated switchgears, sulphur hexafluoride ($SF_6$) is typically used as insulation medium and/or arc-quenching medium, respectively.

Recently, the use of organofluorine compounds in an insulation medium has been suggested as a substitute for conventional insulation media. Specifically, WO-A-2010/142346 discloses a dielectric insulation medium comprising a fluoroketone containing from 4 to 12 carbon atoms. Further, WO-A-2012/080246 discloses a fluoroketone containing exactly 5 carbon atoms (hereinafter referred to as "C5K") in a mixture with a dielectric insulation gas component different from said C5K to be particularly advantageous. The fluoroketones disclosed in WO-A-2010/142346 and WO-A-2012/080246 have been shown to have high insulation capabilities, in particular a high dielectric strength, as well as high arc extinction capabilities. At the same time, they have a very low Global Warming Potential (GWP) and very low toxicity.

Notwithstanding the above-mentioned excellent properties of a fluoroketone-containing insulation gas, it has unexpectedly been found that in a device designed for interrupting non-short circuit currents only, specifically in a disconnector or an earthing switch of a conventional design, interruption of even low currents could fail when using a fluoroketone-containing arc-quenching medium. This is due to the fluoroketone being present in relatively low concentrations in these devices, which goes along with relatively poor thermodynamic and transport properties and thus relatively poor cooling efficiency. The problem particularly applies to arc-quenching media that besides the organofluorine compound comprise a carrier or background gas, typically air or an air component. For example, tests have shown that an earthing switch, which repeatedly interrupts an inductive current of 80 A in several tens of miliseconds or less in $SF_6$, failed to interrupt even lower currents in air and $CO_2$ even after more than half a second of arcing, even though a correspondingly larger gap between the contacts has then been achieved.

Thus, the favourable properties inherent to $SF_6$, which allow efficient extinction of the arc at current-zero also at unblown conditions and which further ensure that the arc does not reignite, are not inherent to such gas mixtures containing organofluorine compounds.

The problem of the present invention is to provide an improved device for interrupting non-short circuit currents only, particularly a disconnector or an earthing switch, by using an arc-quenching medium containing an organofluorine compound, said device allowing at the same time a very reliable current interruption. This problem is solved by the subject matter of claim 1. Embodiments are defined in dependent claims or claim combinations and in the description in conjunction with the drawings.

According to claim 1, the present invention relates to a device for interrupting non-short circuit currents only. Respective devices of the state of the art are designed such that the arc generated during interruption is conventionally extinguished by $SF_6$ under unblown conditions, i.e. without actively inducing a gas flow of $SF_6$ as arc-quenching medium.

The device of the present invention comprises at least two contacts movable in relation to each other between a closed state and an open state and defining an arcing region, in which an arc is generated during a current interrupting operation and in which an arc-quenching medium comprising an organofluorine compound is present.

According to the invention, a counter-arcing component is allocated to the arcing region, said counter-arcing component being designed for counteracting the generation of an arc and/or for supporting the extinction of an arc.

As mentioned, the device of the present invention is designed for interrupting non-short circuit currents only. Particularly herein, the term "short-circuit currents", as opposed to non-short circuit currents, is thereby defined as currents that are established in the first, transient phase of up to approximately 3 seconds after the point in time, when from a grid operated under high voltage the parts under high voltage get connected to ground. According to this definition, the term "non short-circuit currents" relates to any currents not falling under the definition of "short-circuit currents" given above.

A short circuit is an electrical circuit that allows a current to travel along an unintended path, often where essentially no or a very low electrical impedance is encountered. In general, such short-circuit currents must be interrupted within less than 5 seconds after their occurrence and preferably quicker (e.g. within less than 3 seconds) to prevent damages in electrical networks.

According to the present invention, currents that flow from an electrical network (in particular high-voltage network or medium-voltage network) to ground via unintendend or intended paths and last longer than 3 seconds or longer than 5 seconds, are considered "non short-circuit currents". This definition of non-short-circuit currents is based on their duration only and is independent of their magnitude or the intendedness or unintendedness of their occurrence. In particular, this definition of non-short-circuit currents includes nominal currents and excludes short-circuit currents of shorter than 5 seconds duration.

For example, such non-short-circuit currents can be currents that are induced between two parallel overhead lines, wherein one line is on both sides connected to ground and the other line is delivering current to loads. The non-short-circuit currents induced in the grounded overhead line can be interrupted by the devices according to the present invention.

Specifically, the device is a disconnector, in particular a high voltage disconnector, or an earthing switch, in particular a make-proof earthing switch.

According to a further aspect, the present invention also relates to a low voltage circuit breaker comprising at least two contacts movable in relation to each other between a closed state and an open state and defining an arcing region, in which an arc is generated during a current interrupting operation and in which an arc-quenching medium comprising an organofluorine compound is present, wherein to the arcing region a counter-arcing component is allocated and is designed for counteracting the generation of an arc and/or for supporting the extinction of an arc.

The present invention takes into account the surprising finding that inspite of the high dielectric insulation performance of the organofluorine compound, which is preferably used in combination with a carrier gas and more preferably with synthetic air or a gas mixture containing $O_2$ and $CO_2$, the cooling efficiency of an arc-quenching medium containing an organofluorine compound is often insufficient for efficient arc extinction under free-burning conditions.

In contrast to conventional disconnectors, earthing switches or low voltage circuit breakers (low voltage shall typically be below few kV and in particular below 1 kV), in which the cooling efficiency of the arc extinction medium (e.g. $SF_6$) suffices to extinguish the arc under free-burning conditions, the cooling insufficiency of the organofluorine compound-containing arc-quenching medium is compensated for by the presence of the counter-arcing component.

Consequently, potential arc extinction failures can reliably be circumvented also when using a non-$SF_6$ arc-quenching medium comprising an organofluorine compound, which is favourable due to its environmental friendliness and low toxicity. Tus, the present invention allows using these non-$SF_6$ quenching media in devices for interrupting non-short circuit currents only and ensures a very safe operation of these devices.

It is understood that the embodiments described herein both relate to the device for interrupting non-short circuit currents only, specifically to the disconnector or earthing switch, as well as to the low voltage circuit breaker.

According to embodiments, the counter-arcing component comprises or consists of an arc-cooling element for cooling the arc. In combination with the intrinsic cooling properties of the arc-quenching medium, a combined cooling effect is achieved that allows reliable current interruption.

According to further embodiments, the counter-arcing component is designed to be activated during a relative movement of the contacts from closed state to open state.

In particular embodiments, the counter-arcing component can comprise a flow-generating chamber, which is fluidically connected to the arcing region by a flow channel and which is designed such that during a relative movement of the contacts from a closed state to an open state a differential pressure is generated in the flow-generating chamber in relation to the arcing region, said differential pressure causing a flow of the arc-quenching medium between the arcing region and the flow-generating chamber to take place. According to this embodiment, the arc-quenching medium is blown into the arcing region only when the arc is generated, i.e. when the contacts are under voltage and are moved relative to each other from the closed state to the open state and form an arc in the arcing region between the contacts.

According to a very straightforward preferred design, at least one of the contacts forms a piston, which is slideably contained by a guiding tube forming a cylinder, the piston together with the cylinder defining a compression chamber as the flow-generating chamber, said compression chamber being designed to be compressed during a relative movement of the contacts from a closed state to an open state. Specifically, the relative movement of the contacts is directly translated into a flow of the arc-quenching medium into the arcing region for extinction of the arc.

According to further embodiments, the connection between the arcing region and the compression chamber is such that during compression, the arc-quenching medium contained in the compression chamber is ejected into the arcing region.

It is in this regard particularly preferred that the flow channel is formed axially within the piston. This allows for a very straightforward design and further ensures that the distance, which has to be passed by the arc-quenching medium from the compression chamber to the arcing region, is kept as short as possible.

A particularly high blowing speed of the arc-quenching gas can be achieved, if a valve 44 is allocated to the flow channel, said valve 44 opening when a threshold differential pressure is exceeded. The differential pressure particularly relates to the pressure difference between the arcing region and the flow-generating chamber, in particular compression chamber.

According to specific embodiments, the contact forming the piston is a plug contact designed to be slideably engaged within a tulip contact.

According to further specific embodiments, the contact forming the piston is a tulip contact designed to engage around a plug contact. In this regard, the flow channel can be formed as a channel with circular cross-section running parallel to the axis of the tulip contact.

For example, the flow channel is in the form of a flow gap arranged between the inner wall of the tulip contact and the outer wall of a cylindrical flow guide which is radially enclosed by the tulip contact in a spaced-apart manner. The flow channel according to this embodiment has in cross-section an annular form. More specifically, the inner wall of the tulip contact and the outer wall of a cylindrical flow guide run concentrically and parallel to each other, in which case the flow gap has a continuous cross-section over the axial length of the flow guide. More specifically, the flow guide can be formed as an insert fixed to the tulip contact. The presence of a flow guide allows to guide (or "steer") the flow of the arc-quenching medium in a manner such that an even more efficient cooling of the arc is achieved.

Alternatively or additionally, the tulip contact is radially enclosed by a nozzle in a spaced-apart manner, thus forming a nozzle gap which opens out into the arcing region. The nozzle can in particular be a nozzle made of polytetrafluoroethylene (PTFE; Teflon®).

According to further embodiments, the contact forming the piston comprises a proximal contacting region and a distal compressing region arranged axially opposite to the contacting region, wherein the cross-sectional area of the compressing region is larger than the cross-sectional area of the contacting region. By the compressing region having a larger cross-sectional area, a higher pressure can be generated in the compression chamber, allowing for a high blowing speed of the arc-quenching medium and thus a high cooling efficiency to be achieved.

According to still further embodiments, one of the contacts is in the form of a piston and is contained in the other contact, which forms a cylinder for the piston, and the piston is slideably moveable in the cylinder in a gas-tight manner. Thereby, the piston and the cylinder together form a suction chamber as the flow-generating chamber, said suction chamber being designed to increase in volume during a relative movement of the contacts from a closed state to an open state. Thus, flow of the arc-quenching medium to be blown into the arcing region is according to this embodiment generated by suction.

In embodiments, the piston comprises in the region of its front end facing the other contact an electrically insulating nose, specifically in the form of an insulating plug. The insulating nose allows the differential pressure between the arcing region and the suction chamber to be further increased. Owing to the high differential pressure, very high blowing speeds of the arc-quenching medium can be achieved. In particular regarding this embodiment, a high speed of contact movement or stroke shall be provided. For this purpose, a spring element is preferably allocated to at least one moveable contact.

With regard to the above described embodiments, in which the piston and the cylinder together form a suction chamber as the flow-generating chamber, the device can preferably further comprise a control volume designed to be expanded during a relative movement of the contacts from a closed state to an open state, said control volume being in the open state fluidically connected with the arcing region by at least one vent running through the wall of the cylinder. As the contact forming the cylinder, specifically the tulip contact, is pulled back, the arc-quenching medium is allowed to flow out through the vent; the building up of pressure within the cylinder, which might counteract the flow of arc-quenching medium, can thus be avoided. It is thereby particular preferred that the control volume is arranged radially outside of the cylinder.

According to further embodiments, an ablating material, such as PTFE, is arranged adjacent to the contacts, the ablating material being designed to form ablation when exposed to an arc. When the arc is produced, it ablates the ablating material, specifically PTFE, which leads to additional pressure build-up in the arcing region. Without wanting to be bound by theory, it is further assumed that when the arc is produced, turbulence is created, which further cools the arc and hence enhances arc extinction.

With regard to the above described embodiments, in which the flow-generating chamber is a compression chamber and a nozzle made of ablating material, in particular PTFE, is provided, the nozzle can further serve as a flow guide for guiding the arc-quenching medium to the arcing region for optimal cooling.

With regard to the above described embodiments, in which the flow-generating chamber is a suction chamber and the ablating material preferably forms an electrically insulating nose, the arc burning directly over the insulating nose can generate additional over-pressure by material ablation, said over-pressure being proportional to the current. If in addition a nozzle is present, the nozzle can be shaped to adjust the flow in the nozzle region, which can be of advantage to avoid excessive pressure build up.

Additionally or alternatively, the device can comprise as a counter-arcing component a magnet generating a permanent magnetic field in the arcing region. This allows the arc to be moved or rotated and also to be pushed out of the periphery, which causes longer arc lengths and thus higher arc voltage drops and thereby improves extinction of the arc. In specific embodiments, the magnet generates a permanent magnetic field in the arcing region.

As also mentioned above, a spring element is preferably allocated to at least one moveable contact. In specific embodiments, the contacts are held off from transiting from a closed state to an open state by a holding force, and the spring element is designed to build up a spring force exceeding the holding force at a specific point in time. In particular, the one of the contacts can be in the form of a plug contact having a bulge, said bulge holding the plug contact off from axial movement by a respective inward protrusion formed on the other contact, typically a tulip contact. When the spring force exceeds a threshold value, the bulge forces the wall of the tulip contact towards an outward direction and thereby ultimately allows the plug contact to rebound axially out of the tulip contact. Thus, the moving contact, specifically the plug contact, is released at relatively high speed and further counteracts the generation of an arc and/or supports the extinction of an arc during current interruption.

According to further embodiments, one of the contacts is in the form of a piston and is contained in the other contact, which forms a cylinder for the piston, and the piston is slideably moveable in the cylinder, wherein the piston comprises in the region of its front end facing the other contact a resistive element which in axial direction of the piston is sandwiched between two regions of a material of lower resistance. In the closed state, the resistive element is in parallel with the regions of lower resistance and, given that the resistance of the resistive element is much higher, the current flows through the regions of lower resistance. When moving the contacts from the closed state to the open state, the resistances of the resistive element and the regions of lower resistance are in series and are dominated by the resistance of the resistive element. During the arc formation, the total resistance is thus approximately given by the sum of the resistances of the resistive element and the arc. During the opening process, the current in the circuit is low because of the resistive element and hence the arc voltage is increased (compared to without resistive element), which is favourable for arc extinction.

The effect achieved by the present invention is of particular relevance in embodiments, in which the arc-quenching medium further comprises air or at least one air component, in particular selected from the group consisting of: oxygen ($O_2$) and nitrogen ($N_2$), carbon dioxide ($CO_2$), and mixtures thereof. The air or air component functions as a carrier gas or background gas additionally present to the organofluorine compound. As discussed above, the present invention achieves safe operation of the device despite of the relatively poor cooling efficiency of the carrier gas.

According to embodiments, the arc-quenching medium comprises carbon dioxide and oxygen. It is thereby particularly preferred that the ratio of the amount of carbon dioxide to the amount of oxygen ranges from 50:50 to 100:1. It is further preferred that the ratio of the amount of carbon dioxide to the amount of oxygen ranges from 80:20 to 95:5, more preferably from 85:15 to 92:8, even more preferably from 87:13 to less than 90:10, and in particular is about 89:11. In this regard, it has been found on the one hand that oxygen being present in a molar fraction of at least 5% allows soot formation to be prevented even after repeated current interruption events with relatively high current arcing. On the other hand, oxygen being present in a molar fraction of at most 20% (i.e. of 20% or less), more particularly of at most 15% (i.e. of 15% or less), reduces the risk of degradation of the material of the device by oxidation.

According to embodiments of the present invention, the organofluorine compound is selected from the group consisting of fluoroethers (including oxiranes), in particular hydrofluoromonoethers, fluoroketones, in particular perfluoroketones, fluoroolefins, in particular hydrofluoroolefins, fluoronitriles, in particular perfluoronitriles, and mixtures thereof.

In embodiments, the arc-quenching medium can comprise a hydrofluoromonoether containing at least three carbon atoms. A more detailed description of such hydrofluoromonoethers is for example given in WO 2012/080222, the disclosure of which is hereby incorporated by reference in its entirety.

In embodiments, the arc-quenching medium can comprise a fluoroketone containing from four to twelve carbon atoms, preferably containing exactly five carbon atoms or exactly six carbon atoms, or a mixture thereof. A more detailed description of such fluoroketones is for example given in WO 2010/142346, the disclosure of which is hereby incorporated by reference in its entirety.

According to more specific embodiments, the fluoroketone is a perfluoroketone, and more particularly has the molecular formula $C_5F_{10}O$, i.e. it is fully saturated without any double or triple bonds between carbon atoms. The fluoroketone may more preferably be selected from the group consisting of: 1,1,1,3,4,4,4-heptafluoro-3-(trifluoromethyl)butan-2-one (also named decafluoro-2-methylbutan-3-one), 1,1,1,2,3,3,4,4,5,5-decafluoropentan-2-one, 1,1,1,2,2,4,4,5,5,5-decafluoropentan-3-one and octafluorocylcopentanone, and most preferably is 1,1,1,3,4,4,4-heptafluoro-3-(trifluoromethyl)butan-2-one.

1,1,1,3,4,4,4-heptafluoro-3-(trifluoromethyl)butan-2-one can be represented by the following structural formula (I):

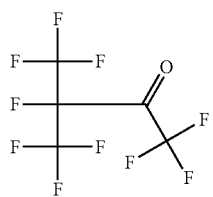

(I)

1,1,1,3,4,4,4-heptafluoro-3-(trifluoromethyl)butan-2-one, herein briefly referred to as "C5K", with molecular formula $CF_3C(O)CF(CF_3)_2$ or $C_5F_{10}O$, has been found to be particularly preferred for high and medium voltage insulation applications, because it has the advantages of high dielectric insulation performance, in particular in mixtures with a dielectric carrier gas, has very low GWP and has a low boiling point. It has an Ozone Depletion Potential (ODP) of 0 and is practically non-toxic.

Additionally or alternatively, the insulation medium can contain 1,1,1,2,4,4,5,5,5-nonafluoro-2-(trifluoromethyl)pentan-3-one (also named dodecafluoro-2-methylpentan-3-one), which can be represented by the following structural formula (II):

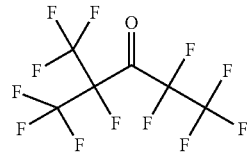

(II)

1,1,1,2,4,4,5,5,5-Nonafluoro-4-(trifluoromethyl)pentan-3-one (here briefly referred to as "C6K") with molecular formula $C_2F_5C(O)CF(CF_3)_2$ has been found to be particularly preferred for high voltage insulation applications because of its high insulating properties and its extremely low GWP. Specifically, its pressure-reduced breakdown field strength is around 240 kV/(cm*bar), which is much higher than the one of air having a much lower dielectric strength ($E_{cr}$=25 kV/(cm*bar)). It has an ozone depletion potential of 0 and is non-toxic. Thus, the environmental impact is much lower than when using $SF_6$, and at the same time outstanding margins for human safety are achieved.

In additional or alternative embodiments, the arc-quenching medium comprises at least one compound being a hydrofluoroether selected from the group consisting of: hydrofluoro monoether containing at least three carbon atoms; hydrofluoro monoether containing exactly three or exactly four carbon atoms; hydrofluoro monoether having a ratio of number of fluorine atoms to total number of fluorine and hydrogen atoms of at least 5:8; hydrofluoro monoether having a ratio of number of fluorine atoms to number of carbon atoms ranging from 1.5:1 to 2:1; pentafluoro-ethyl-methyl ether; 2,2,2-trifluoroethyl-trifluoromethyl ether; and mixtures thereof.

Additionally or alternatively, the arc-quenching medium can comprise a fluoronitrile as organofluorine compound, in particular a perfluoronitrile. For example, the organofluorine compound can be a fluoronitrile, specifically a perfluoronitrile, containing two carbon atoms, three carbon atoms or four carbon atoms. More particularly, the fluoronitrile can be a perfluoroalkylnitrile, specifically perfluoroacetonitrile, perfluoropropionitrile ($C_2F_5CN$) and/or perfluorobutyronitrile ($C_3F_7CN$). Most particularly, the fluoronitrile can be perfluoroisobutyronitrile (according to the formula $(CF_3)_2CFCN$) and/or perfluoro-2-methoxypropanenitrile (according to the formula $CF_3CF(OCF_3)CN$). Of these, perfluoroisobutyronitrile is particularly preferred due to its low toxicity.

Additionally or alternatively, the arc-quenching medium can comprise a fluoroolefin, in particular a hydrofluoroolefin. More particularly, the fluoroolefin or hydrofluoroolefin, respectively, contains at least three carbon atoms or contains exactly three carbon atoms. According to particularly preferred embodiments, the hydrofluoroolefin is thus selected from the group consisting of: 1,1,1,2-tetrafluoropropene (HFO-1234yf; also named 2,3,3,3-tetrafluoro-1-propene), 1,2,3,3-tetrafluoro-2-propene (HFO-1234yc), 1,1,3,3-tetrafluoro-2-propene (HFO-1234zc), 1,1,1,3-tetrafluoro-2-propene (HFO-1234ze), 1,1,2,3-tetrafluoro-2-propene (HFO-1234ye), 1,1,1,2,3-pentafluoropropene (HFO-1225ye), 1,1,2,3,3-pentafluoropropene (HFO-1225yc), 1,1,1,3,3-pentafluoropropene (HFO-1225zc), (Z)1,1,1,3-tetrafluoropropene (HFO-1234zeZ); also named cis-1,3,3,3-tetrafluoro-1-propene), (Z)1,1,2,3-tetrafluoro-2-propene (HFO-1234yeZ), (E)1,1,1,3-tetrafluoropropene (HFO-1234zeE; also named trans-1,3,3,3-tetrafluoro-1-propene), (E)1,1,2,3-tetrafluoro-2-propene (HFO-1234yeE), (Z)1,1,1,2,3-pentafluoropropene (HFO-1225yeZ; also named cis-1,2,3,3,3 pentafluoroprop-1-ene), (E)1,1,1,2,3-pentafluoropropene (HFO-1225yeE; also named trans-1,2,3,3,3 pentafluoroprop-1-ene), and mixtures thereof.

In embodiments, the device of the present invention can in particular be a high voltage disconnector. More particular, it can be a high voltage disconnector designed for bus charging, in particular rated for a current in the range from 0.1 A to 0.8 A and a voltage in the range from 72.5 kV to 800 kV. Higher ratings may be addressed in the future, as well.

In addition or alternatively, the device can be an earthing switch for a high voltage disconnector, which high voltage disconnector is designed for induced current switching, and in particular is rated for a current of 200 A at most and a voltage of 32 kV at most. Higher ratings may be addressed in the future, as well.

Alternatively, it can be a high voltage disconnector designed for bus transfer switching, and in particular is rated for a current of 1.6 kA at most and a voltage in the range from 10 V to 40 V. Higher ratings may be addressed in the future, as well.

Disconnectors of this type using $SF_6$ as arc-quenching medium are known in the art, but do not comprise any counter-arcing component according to the present invention. Counter-arcing components are nowhere suggested in the art, since the arc cooling properties of the arc-quenching gas is generally considered sufficient for extinguishing the arc under unblown conditions.

According to a further aspect, the present invention also relates to a medium voltage or high voltage gas-insulated switchgear comprising a device as described above.

The present invention is further illustrated by way of the attached figures, of which:

Figure 1A:
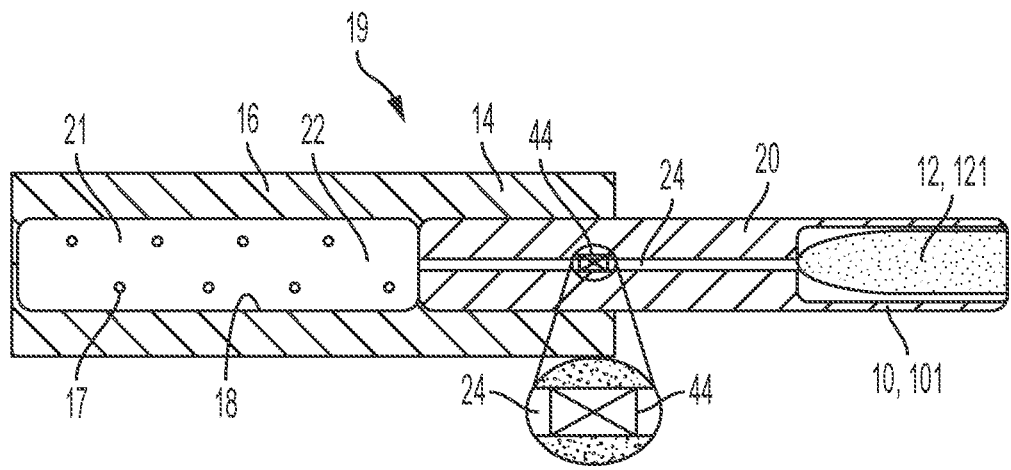
FIGS. 1a, 1b show schematically a counter-arcing component of a first embodiment of the device, the counter-arcing component being activated during a relative movement of the contacts from a closed state shown in FIG. 1a to an open state shown in FIG. 1b.

As shown exemplarily in FIG. 1, the device of the present invention comprises two contacts 10, 12 movable in relation to each other, specifically a first contact 10 in the form of a tulip contact 101, which in the closed position engages around second contact 12 in the form of a plug contact 121.

The tulip contact 101 is slideably contained in a guiding tube 14 forming a cylinder 16 having a continuous inner wall 18. Thus, the tulip contact 101 forms a piston 20, which together with the cylinder 16 defines a compression chamber 22 containing arc-quenching medium 17. Within the piston 20, a flow channel 24 is formed running in axially through the center of the piston 20.

Figure 1B:
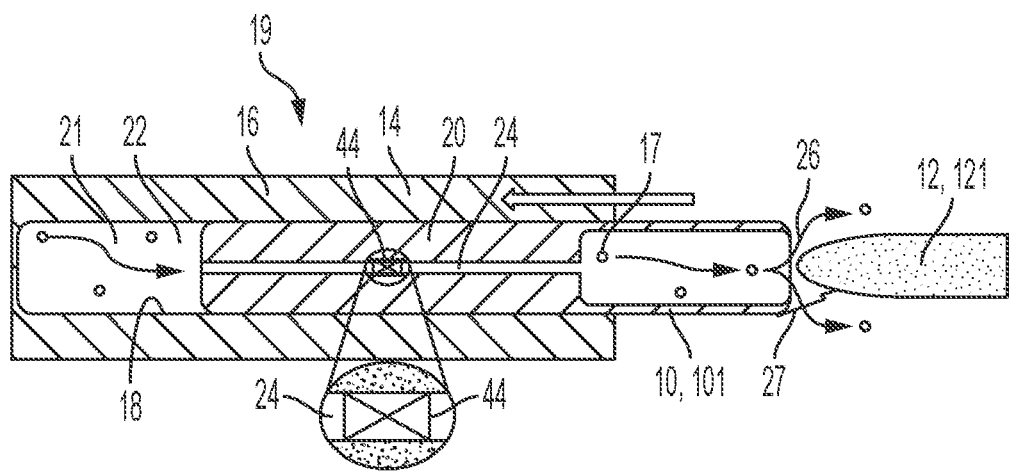

During the movement of the tulip contact 101 from the closed state shown in FIG. 1a to the open state shown in FIG. 1b, the compression chamber 22 is compressed by the piston 20, which moves in direction shown by the arrow in FIG. 1b, and the arc-quenching medium 17 contained in the compression chamber 22 is forced through the flow channel 24 fluidically connecting the compression chamber 22 with the arcing region 26. Thus, arc-extinction medium is ejected into the arcing region 26 at a relatively high blowing speed, which supports extinction of the arc 27.

In other words, a differential pressure between the compression chamber 22 and the arcing region 26 is generated by slideably moving the piston 20 within the guiding tube 14 and hence compressing the compression chamber 22. This causes a flow of the arc-quenching medium 17 from the compression chamber 22 functioning as a flow-generating chamber 21 to the arcing region 26.

The embodiment according to FIGS. 1a, 1b thus comprises a counter-arcing component 19, which comprises a flow-generating chamber 21, in which the flow is generated by compression. Since by increasing the blowing speed, the arc is efficiently cooled, the counter-arcing component functions in this embodiment as an arc-cooling element.

Figure 2A:
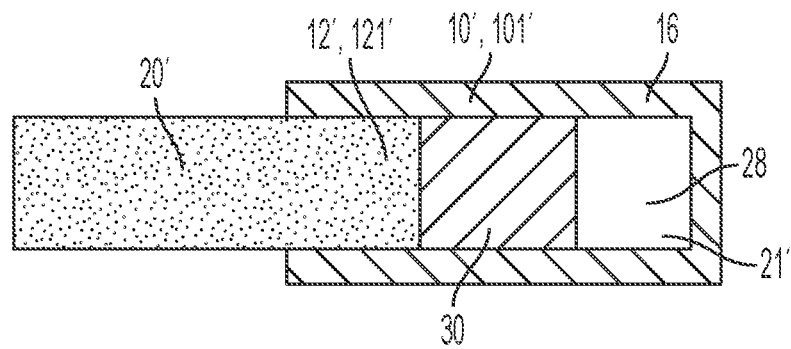
FIGS. 2a, 2b show schematically a counter-arcing component of a second embodiment of the device, the counter-arcing component being activated during a relative movement of the contacts from a closed state shown in FIG. 2a to an open state shown in FIG. 2b.
Figure 2B:
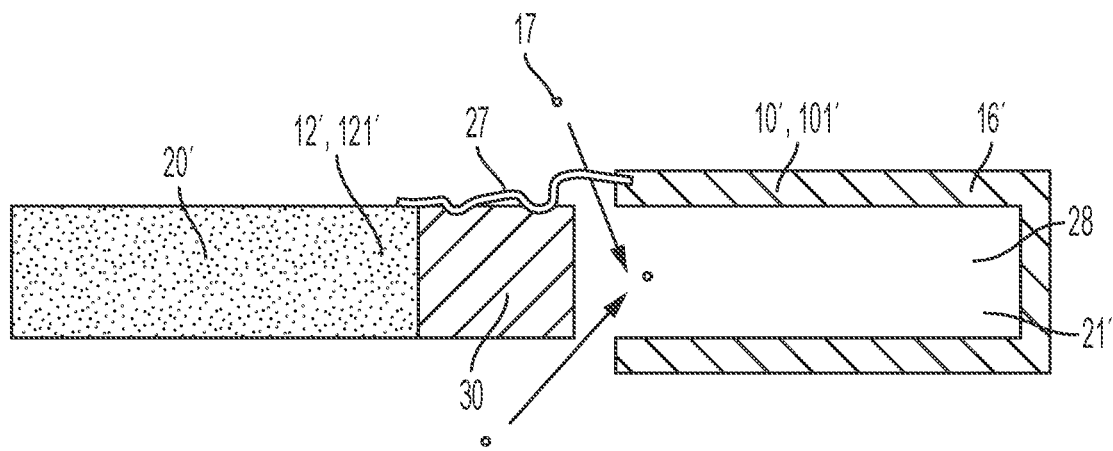

According to the embodiment shown in FIGS. 2a, 2b, a first contact 10' is in the form of a tulip contact 101' in which the second contact 12' in the form of a plug contact 121' is contained. The tulip contact 101' forms a cylinder 16' in which the plug contact 121' forming a piston 20' is slideably moveable in a gas-tight manner. Thus, the piston 20' and the cylinder 16' together form a suction chamber 28 functioning as a flow-generating chamber 21'.

In the region of its front end facing the tulip contact 101', the piston 20' can in particular comprise an electrically insulating nose 30.

During relative movement of the contacts 10', 12' from a closed state shown in FIG. 2a to an open state shown in FIG. 2b, the volume of the suction chamber 28 is increased. At a certain point in the movement, the contacts 10', 12' become separated and the current is interrupted, but the insulating nose 30 of the piston 20' still remains at least to a certain part inside the suction chamber 28. By further moving the piston 20' in the direction away from the cylinder 16', the differential pressure is further increased, owing to the insulating nose 30 functioning as a plug prohibiting pressure equalization. In this state, the arc 27 burns directly over the insulating nose 30, whereby additional over-pressure is generated by material ablation, which further contributes to an even higher differential pressure between the arcing region 26 and the suction chamber 28. At the moment, when the insulating nose 30 is finally released from the cylinder 16', the arc-quenching medium 17 thus flows into the suction chamber 28 at a very high flowing speed generated by the high differential pressure. Ultimately, a strong blowing effect is achieved by the arc-quenching medium 17 flowing at high speed across the arcing region 26, and extinction of the arc 27 is thereby supported.

Figure 3A:
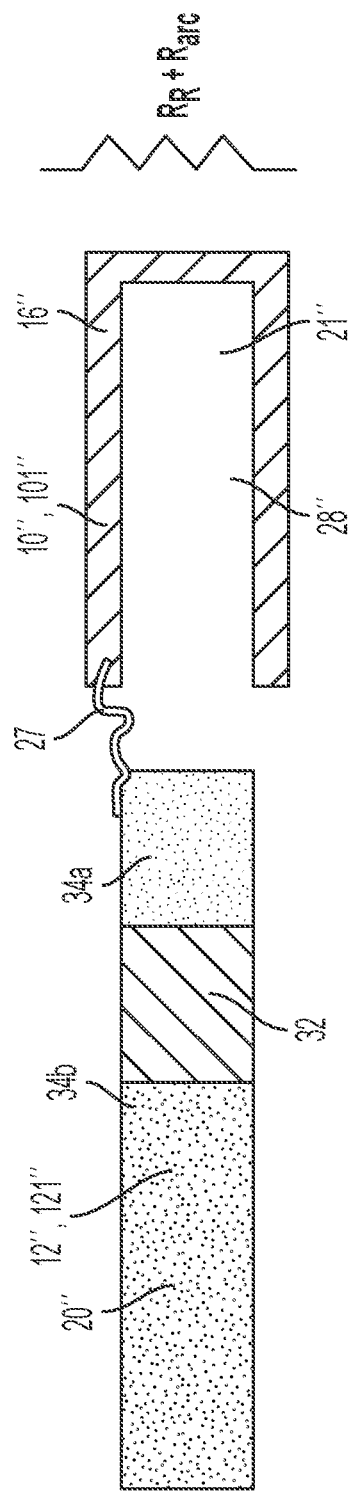
FIGS. 3a, 3b show schematically a counter-arcing component of a third embodiment of the device, the counter-arcing component being activated during a relative movement of the contacts from a closed state shown in FIG. 3a to an open state shown in FIG. 3b.
Figure 3B:
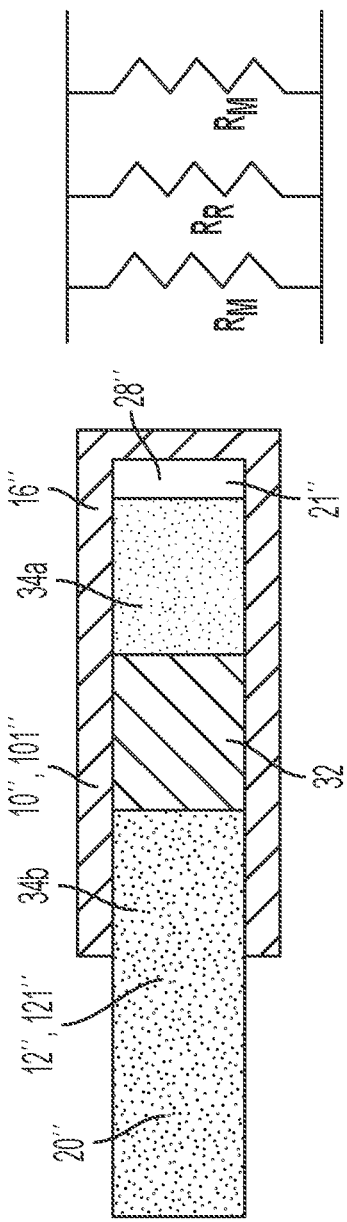

Similarly to the embodiment shown in FIGS. 2a, 2b, also the embodiment shown in FIGS. 3a, 3b comprises a first contact 10" in the form of a tulip contact 101" forming a cylinder 16", in which a second contact 12" in the form of a plug contact 121" forming a piston 20" is slideably moveable in a gas-tight manner. Also in this embodiment, the piston 20" and the cylinder 16" together form a suction chamber 28", which functions as a flow-generating chamber 21".

In distinction to the embodiment shown in FIGS. 2a, 2b, the piston 20" of FIGS. 3a, 3b comprises in the region of its front end facing the tulip contact 101" a resistive element 32 which in axial direction of the piston 20" is sandwiched between two regions 34a, 34b of a lower-resistance material.

In the closed state, the resistive element 32 is in parallel with the regions 34a, 34b of lower resistance, as schematically shown on the right hand side of FIG. 3a. As the resistance of resistive element 32 is much higher, the current flows through the lower-resistance regions 34a, 34b.

When moving the contacts 10", 12" from the closed state shown in FIG. 3a to the open state shown in FIG. 3b, the resistances $R_M$ and $R_M$ of the lower-resistance regions 34a, 34b and $R_R$ of the resistive element 32 get to be in series, as schematically shown on the right hand side of FIG. 3b, and are thus dominated by the resistance $R_R$ of the resistive element 32. During formation of the arc 27, the total resistance is thus given (in good approximation) by the sum of the resistances $R_R$ of the resistive element 32 and $R_{arc}$ of the arc 27. During the opening process, the current in this current path is low because of the resistive element 32, and hence the arc voltage drop may become higher than it would be without resistive element 32, which favourably supports arc extinction.

Figure 4:
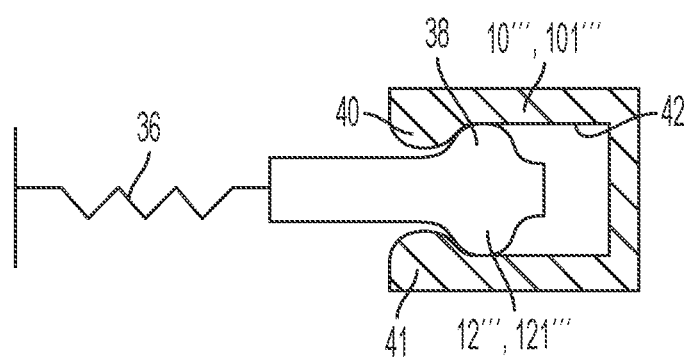
FIG. 4 shows schematically two contacts of an exemplary device with a spring element being allocated to one of the contacts.

The blowing effect achieved by the device of the present invention, in particular of the embodiments shown above, can further be increased by a spring element as shown in FIG. 4. Therein, a first contact 10''' is in the form of a tulip contact 101''', whereas the second contact 12''' is in the form of a plug contact 121''', as for the embodiments shown above. However, in the embodiment of FIG. 4, the plug contact 121''' has a bulge 38, which holds the plug contact 121''' off from axial movement away from the tulip contact 101'''.

To this end, a respective inward protrusion 40 is formed on the inside area 42 of the tulip contact 101'''.

When pulling the contacts 10''', 12''' in a direction away from each other, a point is achieved when the spring force 36 or pulling force 36 exceeds the holding force between the contacts 10''' or 101''' and 12''' or 121''', respectively. At this point, the bulge 38 forces the wall 41 of the tulip contact 101''' in an outward direction, ultimately allowing the plug contact 121''' to rebound axially out of the tulip contact 101'''. Thus, the plug contact 121''' is released at relatively high speed and further counteracts the generation of the arc and/or supports the extinction of the arc during current interruption.

LIST OF REFERENCE NUMERALS 10, 101; 10', 101'; 10", 101"; 10''', 101''' first contact, tulip contact
12, 121; 12', 121'; 12", 121"; 12''', 121''' second contact, plug contact
14 guiding tube
16, 16', 16" cylinder
17 arc-quenching medium
18 inner wall of cylinder
19 counter-arcing component
20, 20', 20" piston
21, 21', 21" flow-generating chamber
22 compression chamber
24 flow channel
26 arcing region
27 arc
28, 28" suction chamber
30 electrically insulating nose
32 resistive element of resistance value $R_R$
34a, 34b regions of piston made of material of lower resistance values $R_M$
36 spring element
38 bulge
40 inward protrusion
41 wall of the tulip contact
42 inside area of tulip contact
44 flow channel valve
$R_{arc}$ arc resistance

The invention claimed is:

1. A device for interrupting non-short-circuit currents only, the device comprising:
   at least two contacts movable in relation to each other between a closed state and an open state and defining an arcing region, in which an arc is generated during a current interrupting operation and in which an arc-quenching medium comprising an organofluorine compound is present, wherein
   a counter-arcing component is allocated to the arcing region and is designed for counteracting the generation of the arc and/or is designed for supporting extinction of the arc, wherein
   one of the contacts is in the form of a piston contained by the other contact forming a cylinder and being slideably moveable in the cylinder in a gas-tight manner, the piston and the cylinder together forming a suction chamber as the flow-generating chamber, said suction chamber being designed to increase in volume during a relative movement of the contacts from a closed state to an open state.

2. The device according to claim 1, wherein the device is a disconnector.

3. The device according to claim 1, wherein the counter-arcing component is configured to be activated during a relative movement of the contacts from a closed state to an open state.

4. The device according to claim 1, wherein the contact forming the cylinder is a tulip contact.

5. The device according to claim 1, wherein the piston comprises an electrically insulating nose in the region of its front end facing the other contact.

6. The device according to claim 1, which further comprises a control volume to be expanded during a relative movement of the contacts from a closed state to an open state, said control volume being in the open state fluidically connected with the arcing region by at least one vent running through the wall of the cylinder.

7. The device according to claim 6, wherein the control volume is arranged radially outside of the cylinder.

8. The device according to claim 1, wherein an ablating material is arranged adjacent to the contacts, the ablating material being adapted to form ablation when exposed to the arc.

9. The device according to claim 1, wherein said counter-arcing component comprises a magnet generating a permanent magnetic field in the arcing region.

10. The device according to claim 1, wherein a spring element is allocated to at least one moveable contact.

11. The device according to claim 10, wherein the contacts are held off from a transition from a closed state to an open state by a holding force and the spring element is adapted to build up a pulling force exceeding the hold force.

12. A medium voltage or high voltage gas-insulated switchgear comprising a device according to claim 1.

* * * * *